United States Patent
Degenhardt et al.

(10) Patent No.: US 8,476,593 B2
(45) Date of Patent: Jul. 2, 2013

(54) PET DETECTOR SYSTEM WITH IMPROVED CAPABILITIES FOR QUANTIFICATION

(75) Inventors: Carsten Degenhardt, Aachen (DE); Andrew Buckler, Wenham, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 6 days.

(21) Appl. No.: 13/319,153

(22) PCT Filed: May 3, 2010

(86) PCT No.: PCT/IB2010/051928
§ 371 (c)(1),
(2), (4) Date: Nov. 7, 2011

(87) PCT Pub. No.: WO2010/140070
PCT Pub. Date: Dec. 9, 2010

(65) Prior Publication Data
US 2012/0061576 A1    Mar. 15, 2012

Related U.S. Application Data

(60) Provisional application No. 61/182,769, filed on Jun. 1, 2009.

(51) Int. Cl.
*G01T 1/10* (2006.01)

(52) U.S. Cl.
USPC ........................................................ 250/362

(58) Field of Classification Search
USPC .................................. 250/362, 363.01–363.1
See application file for complete search history.

(56) References Cited

U.S. PATENT DOCUMENTS

| | | | |
|---|---|---|---|
| 5,773,829 A | 6/1998 | Iwanczyk et al. | |
| 6,856,350 B2 | 2/2005 | Orava et al. | |
| 6,946,658 B2 | 9/2005 | Tai | |
| 2008/0203309 A1* | 8/2008 | Frach et al. | 250/362 |
| 2009/0072156 A1 | 3/2009 | Chinn et al. | |

FOREIGN PATENT DOCUMENTS

| | | |
|---|---|---|
| EP | 1288679 A1 | 3/2003 |
| EP | 102007027921 A1 | 1/2009 |

OTHER PUBLICATIONS

Pollard et al., "Using list-mode data to compare scatter corrections in I-131 imaging," 1992, IEEE, Nuclear Science Symposium and Midical Imaging Conferecne Record, vol. 2, pp. 1111-1113.*
Yoshida et al., "Inter-crystal scatter identification for a depth-sensitive detector using multi-anode outputs," 2006, IEEE Nuclear Science Symposium Conference Record, vol. M06-77, pp. 1860-1864.*
Bentourkia, M., et al.; Nonstationary Scatter Subtraction-Restoration in High-Resolution PET; 1996; The Journal of Nuclear Medicine; 37(12)2040-2046.
Rafecas, M., et al.; Characterization and Processing of Inter-Crystal Scatter in a Dual Layer, High Resolution LSO-APD-PET; 2001; IEEE Nuclear Science Symposium Conference Record; pp. 1128-1132.
Torres-Espallardo, I., et al.; Effect of inter-crystal scatter on estimation methods for random coincidences and subsequent correction; 2008; Phys Med Biol; 53:22391-2411.

* cited by examiner

*Primary Examiner* — Kiho Kim

(57) ABSTRACT

A nuclear medical imaging system employing radiation detection modules with pixelated scintillator crystals includes a scatter detector (46) configured to detect and label scattered and non-scattered detected radiation events stored in a list mode memory (44). Coincident pairs of both scattered and non-scattered radiation events are detected and the corresponding lines of response (LOR) are determined. A first image representation of the examination region can be reconstructed using the LORs corresponding to both scattered and non-scattered detected radiation events to generate a lower resolution image (60) with good noise statistics. A second higher resolution image (62) of all or a subvolume of the examination region can be generated using LORs that correspond to non-scattered detected radiation events. A quantification processor is configured to extract at least one metric, e.g. volume, count rate, standard uptake value (SUV), or the like, from at least one of the lower resolution image, the higher resolution image, or a combined image (64).

19 Claims, 3 Drawing Sheets

PET DETECTOR SYSTEM WITH IMPROVED CAPABILITIES FOR QUANTIFICATION

CROSS REFERENCE TO RELATED APPLICATIONS

This application claims the benefit of U.S. provisional application Ser. No. 61/182,769 filed Jun. 1, 2009, which is incorporated herein by reference.

The following relates to the radiation detector arts. It finds particular application in conjunction with radiation detectors for nuclear medical imagers employing radiation transmission or radiopharmaceuticals, such as single photon emission computed tomography (SPECT) imagers and positron emission tomography (PET) imagers as well as planar x-ray imagers, radio-astronomy, and the like, and will be described with particular reference thereto. It will be appreciated that the invention may also be applicable to other radiation detector modalities, and in systems and methods employing radiation detectors.

In single-photon emission computed tomography (SPECT), a radiopharmaceutical is administered to an imaging subject, and one or more radiation detector arrays, commonly called gamma cameras, are used to detect the radiopharmaceutical via radiation emission caused by radioactive decay events. Typically, each gamma camera includes a radiation detector array and a collimator disposed in front of the radiation detector array. The gamma cameras are moved over a range of angular views, for example over a 180° or 360° angular range, and the resulting projection data can be reconstructed using filtered back-projection, expectation-maximization, or another imaging technique into an image of the radiopharmaceutical distribution in the imaging subject. Advantageously, the radiopharmaceutical can be designed to concentrate in selected tissues to provide preferential imaging of those selected tissues.

In positron emission tomography (PET), a radiopharmaceutical is administered to the imaging subject, in which the radioactive decay events of the radiopharmaceutical produce positrons. Each positron interacts with an electron to produce a positron-electron annihilation event that emits two oppositely directed gamma ($\gamma$) rays. Using coincidence detection circuitry, a ring array of radiation detectors surrounding the imaging subject detect the coincident oppositely directed gamma ray events corresponding to the positron-electron annihilation(s). A line of response (LOR) connecting the two coincident detections intersects the position of the positron-electron annihilation event. Such lines of response are analogous to projection data and can be reconstructed to produce a two- or three-dimensional image. In time-of-flight PET (TOF-PET), the small time difference between the detection of the two coincident $\gamma$ ray events is used to localize the annihilation event along the LOR.

In planar x-ray imaging, a radiation source irradiates an imaging subject, and a radiation detector array disposed on the opposite side of the imaging subject detects the transmitted radiation. Due to attenuation of radiation by tissues in the imaging subject, the detected radiation provides a two-dimensional planar representation of bones or other radiation-absorbing structures in the imaging subject. Such transmission-based imaging is improved upon in transmission computed tomography imaging, in which the x-ray tube or other radiation source is moved around the imaging subject to provide transmission views or projection data over an extended angular range, for example over a 180° or 360° span of angular views. Using filtered back-projection or another image reconstruction technique, this radiation projection data is reconstructed into a two- or three-dimensional image representation.

SPECT and PET radiation detector modules have traditionally included an array of photomultiplier tubes (PMT's) optically coupled with an array of scintillator crystals using an intermediate light guide layer. The scintillator crystal converts the absorbed radiation particle into a light burst which is detected and localized by a plurality of photomultiplier tubes using Anger logic. In some radiation detection systems, the photomultiplier tubes have been replaced by photodiodes that produce an analog signal proportional to the intensity of the received light. Photodiodes offer a cost-effective, low voltage alternative to photomultiplier tubes in high light situations. Silicon photomultipliers (SiPM) detectors have been developed which incorporate the high gain and stability of photomultiplier tubes along with the cost-effective, low voltage nature of the analog photodiodes.

Rather than using Anger logic, which suffers from event mispositioning due Compton scatter, count rate saturation, and non-linear response (pile-up effects), pixelated scintillator detectors have been proposed. In a pixelated detector, there is typically a 1:1 matching of individual scintillator crystals and photodiode pixels. Detection location is determined by the location of the pixelated detector which detects the $\gamma$ ray event.

In the case of LYSO as the scintillator crystal, approximately 30% of the radiation events are scattered. In a PET scanner with two detectors per LOR, about half of the LORs are associated with a scattered event at least at one end. That is, a radiation event strikes a first pixelated scintillator, causes a scintillation, and is Compton scattered in to a second scintillator where it causes another scintillation. The scattered radiation can undergo further Compton scattering in yet additional pixelated scintillators. Similarly in larger crystals associated with Anger logic systems, a single $\gamma$ event can be Compton scattered causing a plurality of scintillations. Compton scatter leads to ambiguous even location and reduced spatial resolution. Scattered events are characterized by lower amplitudes. Filtering or removing scattered events reduces the number of events for reconstruction by 30-50%. The temporal proximity of the Compton scattered events can cause them to appear as a single, blurred event to PMTs.

Energy windowing, pulse shape analysis, and other filtering methods have been developed to improve spatial resolution; however, the increased computation time required generally limits the filtering to qualitative analysis, e.g. a physician diagnosing based on an image representation. Quantification schemes are available, e.g. Standard Uptake Value (SUV) is a widely used quantifier in cancer treatment response. The advantage of SUV calculation is that blood samples are not necessary; however, SUV is vulnerable to variability due to image noise, poor resolution, and inadequately defined regions of interest. Compared to Fractional Uptake Rate (FUR), a quantitative alternative requiring blood sample measurements, SUV's can yield opposite conclusions regarding the progression of the disease.

The present application provides a new and improved method and apparatus to improve the spatial resolution of nuclear medical imagers employing pixelated crystal readout and to improve quantification of tomograms which overcomes the above-referenced problems and others.

In accordance with one aspect, a method for nuclear medical imaging is presented. The method includes detecting gamma ($\gamma$) radiation events on one of more radiation detector modules arranged about an examination region. The detected radiation events are discriminated between the scattered and non-scattered events and labeled accordingly. The radiation events are stored in a list mode.

In accordance with another aspect, a nuclear medical imaging system includes at least one radiation detection module to detect radiation events from an examination region. A scatter detector is configured to detect and label both scattered and non-scattered radiation events. A list mode memory stores the detection locations of the detected radiation events with their respective labels.

One advantage is that resolution is improved.

Another advantage is that pile-up is reduced.

Another advantage is that quantitative metrics can be reliably extracted from image representations.

Another advantage is that signal-to-noise ratio is improved.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically shows a nuclear medical imaging system employing radiation detector modules with pixelated scintillator;

Figure 1:
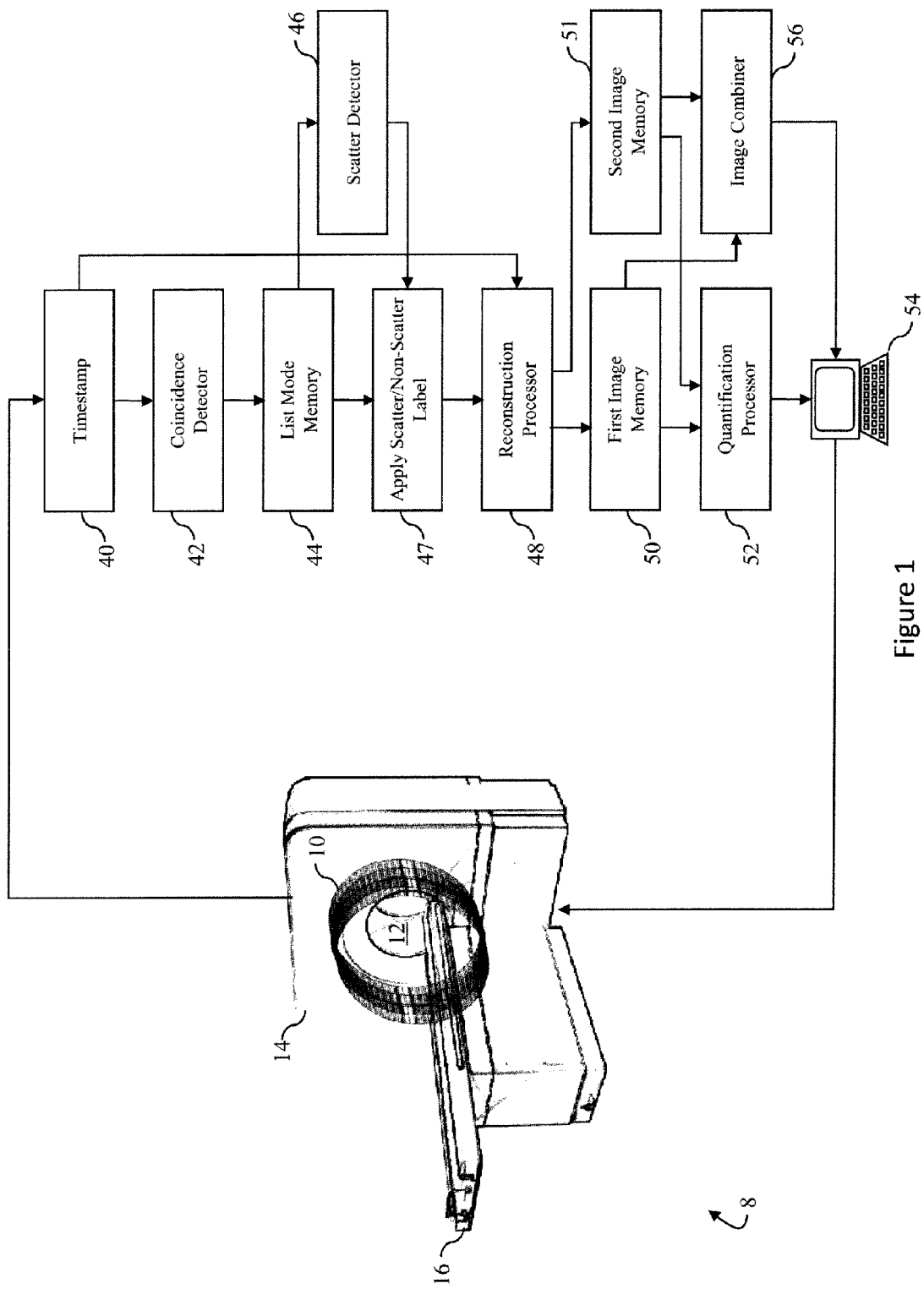

With reference to FIG. 1, a PET or other radiation tomography scanner 8 includes a plurality of radiation detector modules 10 oriented to receive radiation from an imaging region 12. The radiation detector modules 10 are arranged in several adjacent rings along an axial direction; however, other arrangements of radiation detector modules can be used. Typically the radiation detector modules 10 are housed within a housing 14 of the tomography scanner 8 and thus are not visible from the outside. Each ring is comprised of up to hundreds of radiation detector modules 10. In some scanners, only a single ring of radiation detector modules 10 is provided, in others, up to five or more rings of radiation detector modules 10 are provided. It should be appreciated that detector heads can be used in place of the detector ring structure shown in FIG. 1. The tomography scanner 8 includes a subject support 16 for positioning an object or patient in the imaging region 12. Optionally, the support 16 is linearly movable in the axial direction generally transverse to the rings of the radiation detector modules 10 to facilitate acquisition of three-dimensional imaging data over an extended axial distance.

Figure 2:
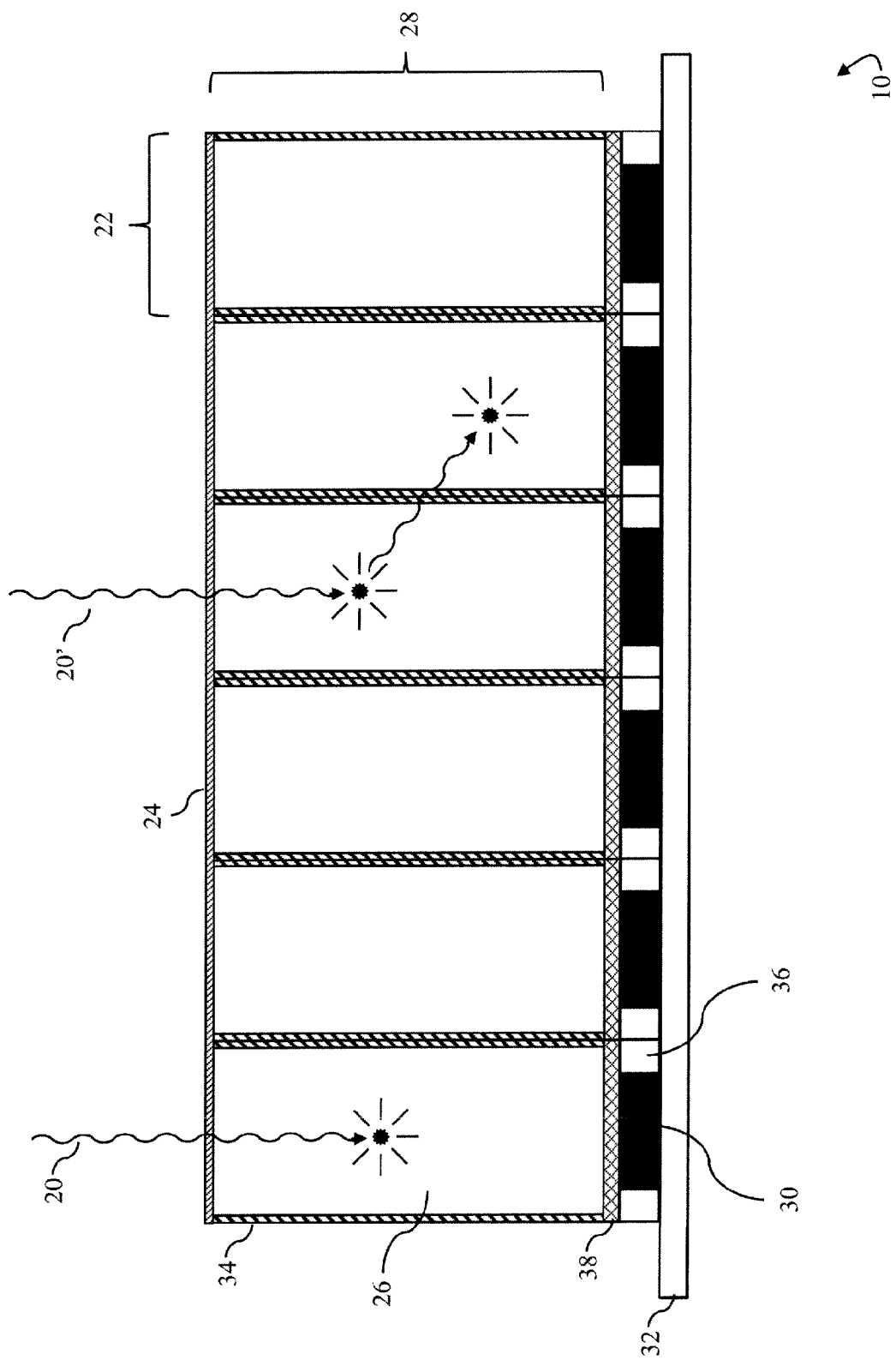
FIG. 2 is a diagrammatic side-view in partial of a radiation detector module with a pixelated scintillator crystal.

With reference to FIG. 2, a radiation detector module 10 is illustrated. When a γ ray 20 strikes a radiation detector module it can interact with one or more individual detector elements 22. First, the γ ray passes through a radiation transmissive layer 24. The radiation transmissive layer 24 allows gamma radiation to pass through with negligible absorption while reflecting light photons. The γ ray then strikes an individual scintillator crystal 26 of a pixelated scintillator 28 that converts the radiation into a plurality of light photons, i.e. a scintillation. The light photons are detected by a photoelectric detector 30 that is made up of an array of photodiodes disposed monolithically on a common silicone substrate 32. The photodiodes can include solid state photomultipliers such as analog photodiodes, digital silicon photomultipliers (SiPMs), or the like. SiPMs offer a stable, high gain, and low-voltage alternative to analog photodiodes. About 30% of the rays 20' interact with a first scintillator generating light photons and are Compton scattered into another scintillator generating more light photons.

Only a fraction of the photons strike the photoelectric detector 30 directly. To increase the number photons reaching the photoelectric detector, the sidewalls of each scintillator crystals 24 are covered with a light reflecting layer 34 such as Teflon®, Vikuiti®, or the like. The light reflecting layer also inhibits photons from entering adjacent scintillator crystals and being detected by the corresponding photoelectric detector. A light reflective spacer 36 is disposed between the adjacent photoelectric detectors to prevent photons from escaping the scintillator crystal without hitting the photoelectric detector. In addition to scatter suppression, pixelating the scintillator crystal reduces pile-up effects which can further enhance image resolution.

Disposed between the scintillator crystals 26 and the photoelectric detectors 28 is an optical coupling layer 38. When light reaches a boundary between materials with different indices of refraction, some of the light will be transmitted while some will be reflected back. Because reflection is not desired between the scintillator crystal and the photoelectric detector, the optical coupling layer 36 is interposed to minimize reflection.

With reference again to FIG. 1, before the nuclear scan commences, a patient on the support 16 is injected with a radiopharmaceutical containing a radioactive element that is typically coupled to a tag molecule. A tag molecule is associated with a region of interest to be imaged, and tends to accumulate in that region via usual body processes. For example, malignant cancer cells tend to consume abnormally high amounts of energy; therefore, radioactive elements are usually coupled to glucose, a molecule that a cell typically metabolizes to create energy. The accumulation of the radiopharmaceutical gathers in such regions and appears as "hot spots" in the image. Other techniques include tagging molecules that reside within the circulatory system for perfusion studies or the like.

The γ rays occurring from the decay of the radiopharmaceutical are detected by the annularly arranged radiation detector modules 10. A trigger circuit (not shown) monitors the photoelectric detectors 28 for an energy pulse, i.e. integrated area under the pulse, characteristic of a scintillation event. A time stamp is associated with each detected scintillation event by a time stamp circuit 40. The trigger circuit and the time stamp circuit can also be integrated into the photoelectric detector substrate. A coincidence detector 42 determines coincident pairs of γ rays and the LOR defined by each coincident pair of γ rays. Coincident pairs are determined by the difference in detection time of the coincidence pairs and the known diameter of the field of view.

The detector locations for the LOR and the corresponding time stamp are stored in a list mode memory 44 as a single entry in a list mode format. A scatter detector 46 determines whether either detected radiation event of a coincident pair is non-scattered or scattered. A non-scattered event is defined as an event in which only one scintillator emits light photons. The scatter detector appends 47 one bit of data to each entry in the list mode memory to indicate whether the detected radiation event underwent scatter or not. To summarize, each entry in the list mode memory indicates detection times, detection locations, and a scatter/non-scatter label for each coincident pair of detected radiation events.

A reconstruction processor 48 reconstructs all the LORs, scattered or not, into a first image representation which is stored in a first image memory 50 and reconstructs the LORs with no scatter into a second image representation which is stored in a second image memory 51. A quantification processor 52 quantifies one or more metrics of a selected region/structure of interest. Metrics can include the volume, count rate, standard uptake value (SUV) of the region/structure of interest. The region/structure of interest is selected by a clinician using a graphic user interface or display device 54. The graphic user interface or display device includes a user input device which a clinician can use to select scanning sequences and protocols, reconstruction methods, display image data, and the like. In a TOF-PET system, the reconstruction processor also derives time-of-flight information for each LOR from the time-stamp circuit 50.

Figure 3:
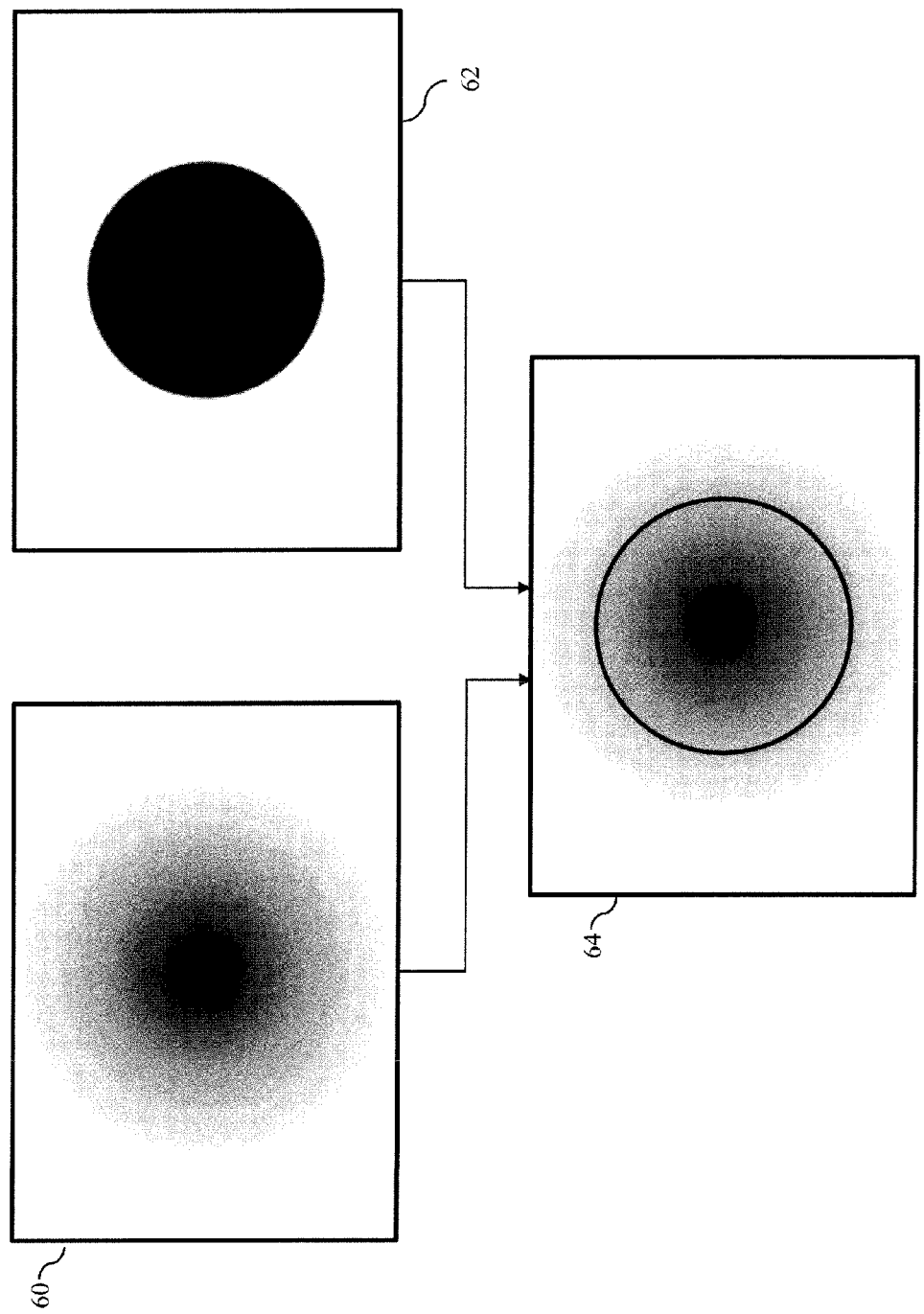
FIG. 3 shows an image combiner that combines the first representation and the second representation into a combined image.

With reference to FIG. 3, an image combiner 56 combines the first image representation 60 and the second image representation 62 into a combined image 64 for concurrent display. For example, the images can be superimposed in different colors, the outline of the second image representation hotspots can be superimposed on the first image representation, the first and second image representations can be displayed side by side with a common scale, or the like.

The first image representation 60 of the examination region which is reconstructed using the lines of response corresponding to both scattered and non-scattered detected radiation events has better noise statistics, but lower resolution. The second image representation 62 of the examination region which is reconstructed using the lines of response corresponding to non-scattered detected radiation events has better resolution, thus allows for detection of small lesions but may not show weak hot spots. Thus, each provides complimentary information. The quantification processor extracts one or more metrics from either the second image representation or the combined image representation 64. The metrics can be displayed alongside the quantified image representation on the graphical user interface or display device.

In another embodiment, a first image representation of the examination region is reconstructed using the lines of response corresponding to both scattered and non-scattered detected radiation events. A clinician selects a subvolume or structure of interest, e.g. a suspicious lesion, in the first image representation. The second image representation is reconstructed using only the lines of response corresponding to non-scattered detected radiation events, which pass through the subvolume, to generate a higher resolution image representation of the subvolume. The combined image representation can take various forms. For example, the non-scattered image of the subvolume can be substituted for the subvolume in the first image. The quantification processor extracts one or more metrics from either the second image representation or the combined image representation. The metrics can be displayed alongside the quantified subvolume image representation on the graphical user interface or display device.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for nuclear medical imaging, comprising:
   detecting gamma ($\gamma$) radiation events on one of more radiation detector modules arranged about an examination region;
   discriminating between scattered and non-scattered detected radiation events;
   reconstructing a first image representation of the examination region using the scattered and non-scattered radiation events;
   selecting a subvolume of interest in the first image representation; and
   reconstructing the subvolume of interest into a second image representation using non-scattered radiation events which correspond to the selected subvolume of interest.

2. The method according to claim 1, wherein each radiation detector module is configured with a pixelated readout scintillator constructed of a plurality of optically isolated scintillator crystals each optically coupled with a a photoelectric detector.

3. The method according to claim 2, wherein the photoelectric detectors include silicon photomultipliers (SiPMs).

4. The method according to claim 1, further including extracting quantitative data from the subvolume of interest based on at least one metric.

5. The method according to claim 4, wherein the metric is chosen from volume, count rate, and standard uptake value (SUV).

6. The method according to claim 1, further including:
   storing the detected events in list mode including an identifier for at least one of the stored scattered and non-scattered events.

7. A method, for nuclear medical imaging, comprising:
   detecting gamma ($\gamma$) radiation events on one of more radiation detector modules arranged about an examination region;
   discriminating between scattered and non-scattered detected radiation events;
   reconstructing a lower resolution first image representation of the examination region using both the scattered and the non-scatter detected radiation events;
   reconstructing a higher resolution second image representation of the examination region using the non-scattered detected radiation events;
   combining the first and second image representations into a combined image representation; and,
   displaying the combined image representation.

8. The method according to claim 7, further including:
   detecting coincident pairs of detected radiation events; and
   determining lines of response corresponding to each coincident pair.

9. The method according to claim 7, further including:
   labeling the detected events as one of scattered and non-scattered;
   storing the detected radiation events in a list mode.

10. A nuclear medical imaging system, including:
    at least one radiation detector module to detect radiation from an examination region;
    a scatter detector which detects and labels both scattered and non-scattered radiation events;
    a list mode memory which stores detection locations of the detected radiation events with their respective scatter/non-scatter labels; and
    at least one processor which reconstructs the detected scattered and non-scattered radiation events into a first image representation and at least some of the non-scattered radiation events into a second image representation, which processes the first and second image representations into a diagnostic image representation for display, and which quantifies at least one metric of a selected structure of interest in one of the diagnostic image representation.

11. The nuclear medical imaging system according to claim 10, wherein the radiation detector module includes:
  a pixelated scintillator constructed of a plurality of optically isolated scintillator crystals; and
  a plurality photoelectric detectors each optically coupled to one of the scintillator crystals.

12. The nuclear medical imaging system according to claim 11, wherein the photoelectric detectors include silicon photomultipliers (SiPMs).

13. The nuclear medical imaging system according to claim 10, further including:
  a plurality of radiation detector modules disposed to detect radiation events from the examination region;
  a time stamp circuit to associate a time stamp with detected radiation events;
  a coincidence detector to detect coincident pairs of detected radiation events and determine lines of response corresponding to each coincident pair; and
  wherein the list mode memory stores detection times, detection locations, and scattered/non-scattered labels for each coincident pair of detected radiation events.

14. The nuclear medical imaging system according to claim 13, wherein the scatter detector is configured to label coincident pairs stored in the list mode memory as non-scatter events if neither detected radiation event of the coincident pair is scattered and to label coincident pairs with at least one scattered detected radiation event as scattered.

15. The nuclear medical imaging system according to claim 13, wherein the label is one bit of data appended to a corresponding list mode entry.

16. The nuclear medical imaging system according to claim 10, wherein the one or more processors combines at least portions of the first and second image representations to generate the diagnostic image representation and further including: an a display which displays the diagnostic image representation.

17. The nuclear medical imaging system according to claim 10, wherein the metric is chosen from volume, count rate, standard uptake value (SUV).

18. A method for nuclear medical imaging, comprising:
  detecting gamma ($\gamma$) radiation events on one of more radiation detector modules arranged about an examination region;
  discriminating between scattered and non-scattered detected radiation events;
  reconstructing a lower resolution first image representation using both the scattered and non-scattered radiation events;
  reconstructing a higher resolution second image representation using at least a portion of the non-scattered radiation events; and
  displaying a combination of the first and seconding image representations.

19. The method according to claim 18, further including:
  labeling the detected events with one of scattered or non-scattered label; and
  storing the detected radiation events in a list mode.

* * * * *